United States Patent [19]
Nakos et al.

[11] Patent Number: 5,266,670
[45] Date of Patent: Nov. 30, 1993

[54] SELECTIVE MONOHYDROSILATION OF VINYL AND ETHYNYL FUNCTIONAL NORBORNENES AND CURABLE PRODUCTS PRODUCED THEREBY

[75] Inventors: Steven T. Nakos, Andover; Anthony F. Jacobine, Meriden; David M. Glaser, New Britain, all of Conn.

[73] Assignee: Loctite Corporation, Newington, Conn.

[21] Appl. No.: 315,737

[22] Filed: Feb. 24, 1989

Related U.S. Application Data

[63] Continuation-in-part of Ser. No. 99,676, Sep. 21, 1987, Pat. No. 4,808,638, which is a continuation-in-part of Ser. No. 917,962, Oct. 14, 1986, abandoned.

[51] Int. Cl.$^5$ .................. C08G 77/20; C07F 7/08
[52] U.S. Cl. ...................................... 528/32; 528/34; 528/40; 556/440; 556/479; 556/489
[58] Field of Search .................. 528/15, 31, 25, 26, 528/32, 34; 556/438, 439, 440, 465, 479, 489

[56] References Cited

U.S. PATENT DOCUMENTS

| | | | |
|---|---|---|---|
| 3,375,236 | 3/1968 | Van de Castle | 526/279 |
| 3,590,065 | 6/1971 | Rakus et al. | |
| 3,746,734 | 7/1973 | Berger et al. | |
| 4,038,302 | 7/1977 | Reichel et al. | 556/479 |
| 4,100,172 | 7/1978 | Mui et al. | |
| 4,340,709 | 7/1982 | Jeram et al. | |
| 4,477,326 | 10/1984 | Lin | |
| 4,507,187 | 3/1985 | Jacobine et al. | |
| 4,534,838 | 8/1985 | Lin et al. | |
| 4,587,276 | 5/1986 | Lien et al. | |
| 4,599,440 | 7/1986 | Watanabe et al. | |
| 4,623,741 | 11/1986 | Watanabe et al. | |
| 4,625,043 | 11/1986 | Saito | |
| 4,640,968 | 2/1987 | Watanabe et al. | |
| 4,665,147 | 5/1987 | Lien et al. | |
| 4,666,953 | 5/1987 | Klemarczyk et al. | |
| 4,699,802 | 10/1987 | Nakos et al. | |
| 4,814,473 | 3/1989 | Kabeta | |
| 4,814,475 | 3/1989 | Funahashi et al. | 556/489 |

FOREIGN PATENT DOCUMENTS

| | | |
|---|---|---|
| 141380 | 5/1985 | European Pat. Off. |
| 2595364 | 9/1987 | France |

OTHER PUBLICATIONS

R. N. Meals, "Hydrosilation in the Synthesis of Organosilanes", Pure & Appl. Chem., 13, 141–157 (1966).
Lukevics, "Latest Research on the Hydrosilation Reaction", Russian Chemical Reviews, 46, 264–277 (1977).
Speier et al., "The Addition of Silicon Hydrides to Olefinic Double Bonds. Part II. The Use of Group VIII Metal Catalysts", J. Am. Chem. Soc., 79, 974–979 (1957).
Rejhon et al., Coll. Chechoslov. Chem. Commun., 40, 3680–3687.
Saam et al., "The Addition of Silicon Hydrides to Olefinic Double Bonds. Part III. The Adddition to Non--terminal Olefins in the Presence of Chloroplantinic Acid", JACS, 80, 4104–4106 (1958).
Petrov et al., Zhurnal Obschei Khimii, 31, #4, 1199, (1961), "The Preparation of Organosilicon Derivatives of Bicyc Lo-(2,2,1)-Heptane"

Primary Examiner—Ralph H. Dean, Jr.
Attorney, Agent, or Firm—Vidas, Arrett & Steinkraus

[57] ABSTRACT

A process comprising the steps of:
1) reacting a norbornene compound of the formula:

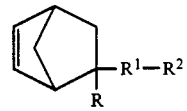

where R is H or methyl, $R^1$ is a direct bond or —C(=O)O— and $R^2$ is vinyl, ethynyl, allyl or propargyl, with a silicon hydride functional compound in the presence of hydrosilation catalyst at a temperature of at least 60 degrees; and
2) recovering a product which consists essentially of the addition products of the silicon hydride functional compound to the $R^2$ group of the norbornene compound and which is substantially free of addition products of the silicon hydride functional compound to the internal ring double bond of the norbornene compound.

The products of this process can be used to produce norbornene functional prepolymers which are useful in cureable silicone formulations based on thiolene or hydrosilation cure chemistry.

10 Claims, No Drawings

SELECTIVE MONOHYDROSILATION OF VINYL AND ETHYNYL FUNCTIONAL NORBORNENES AND CURABLE PRODUCTS PRODUCED THEREBY

This application is a continuation-in-part of application Ser. No. 099,676, filed Sep. 21, 1987, now U.S. Pat. No. 4,808,638, as a continuation-in-part of Ser. No. 917,962, filed Oct. 14, 1986, now abandoned.

BACKGROUND OF THE INVENTION

1. Field of the Invention

In co-pending application Ser. No. 099,676, there are described curable thiolene compositions using norbornenyl functional olefins. The invention of the present application pertains to improved silicone norbornenyl compounds, silane capping agents to produce compounds and thiolene formulations utilizing such compounds.

2. Description of the Prior Art

In Petrov, et al, *Zhurnal Obschei Khimii*, 31, 1199 (1961), there is a description of the hydrosilation of various norbornene compounds, one of which is vinyl norbornene. The vinyl norbornene reaction was run at 30° C. using trichlorosilane. The authors of this reference report that a mixture of products was obtained, the addition taking place at the both the internal double bond of the norbornene ring and at the vinyl group in approximately similar proportions:

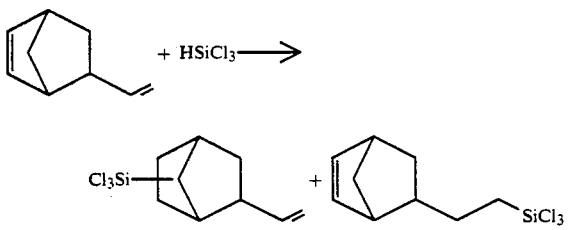

In various references, Watanabe et al, describe hydrosilation reactions of 5-ethylidenebicycylo(2,2,1)hept-2-ene:

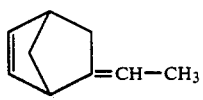

This hydrosilation is only reported to produce addition on the norbornene ring double bond. See for instance U.S. Pat. Nos. 4,599,440; 4,623,741; 4,625,043; and 4,640,968. These reaction products were used to make siloxane monomers for vulcanization to yield silicone elastomers.

From the Petrov et al and Watanabe et al, references persons skilled in the art would conclude that it is not possible to selectively hydrosilate norbornene derivatives containing other unsaturated sites because the norbornene unsaturation itself is reactive under hydrosilation conditions.

SUMMARY OF THE INVENTION

The present invention in one aspect is a novel process comprising the steps of:

1) reacting a norbornene compound of the formula:

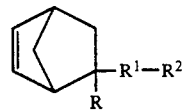

where R is H or methyl, $R^1$ is a direct bond or —C(=O)O— and $R^2$ is vinyl, ethynyl, allyl or propargyl, with a silicon hydride functional compound in the presence of hydrosilation catalyst at a temperature of at least 60° C.; and 2) recovering a product which consists essentially of the addition products of the silicon hydride functional compound to the $R^2$ group of the norbornene compound and which is substantially free of addition products of the silicon hydride functional compound to the internal ring double bond of the norbornene compound.

In one embodiment the silicon hydride functional compound is a silicon hydride functional polysiloxane polymer.

In a preferred embodiment the silicon hydride functional compound is a compound of the formula:

where X is hydrolyzable group, a is 1–3 and $R^3$ is hydrocarbyl.

As a further aspect of the invention there are the compounds:

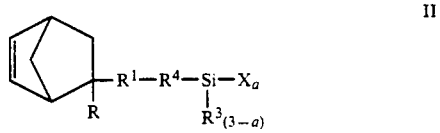

in substantially pure form, where X, R, $R^1$ and $R^3$ are as previously defined and $R^4$ is ethylene, ethenylene, propylene or propenylene.

A further aspect of the invention comprises a polyorganosiloxane polymer containing a plurality of groups of the formula:

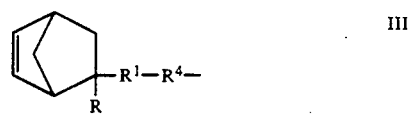

bound to silicon atoms thereof, said polymer being substantially free of groups of the formula:

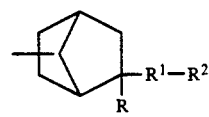

bound to silicon atoms thereof where $R^2$ is vinyl, ethynyl, allyl or propargyl.

A still further aspect of the invention is an improved curable formulation comprising a polymer as set forth in the previous formula, a silicone polythiol or poly-SiH component and an initiator of thiolene or hydrosilation reactions, respectively.

DETAILED DESCRIPTION OF THE INVENTION

The reaction to selectively hydrosilate the side chain unsaturation of the starting norbornene compound is surprisingly straightforward. Using reaction temperatures of at least 60° C., preferably at least 70° C., in the presence of common hydrosilation catalysts, the reaction proceeds exothermically. It is generally desirable that the norbornene compound be in substantial excess on the basis of moles of norbornene compared to equivalents of SiH. Suitably there is a 50% excess. The excess norbornene compound, however, appears desirable more from the standpoint of improving yield by driving the reaction toward completion rather than as a safeguard against non-selective hydrosilation of the norbornene ring double bond. Upon completion of the reaction, the excess norbornene starting compound is readily removed from the reaction mixture by distillation.

The invention will be described and exemplified below primarily with respect to the preferred vinyl norbornene starting material. However, it will be readily seen that similar results may be obtained using other norbornene compounds within the formula given above. Moreover it will be appreciated that modifications of the materials and conditions exemplified herein may readily be made by those skilled in the art without departing from the invention hereof which is set forth in the claims hereof.

SiH functional organosiloxane polymers can be used to directly hydrosilate the norbornene compound. Suitable procedures may be obtained by modifying the examples of U.S. Pat. No. 4,665,147, substituting equivalent weights of vinyl norbornene for the β-(allyloxy)ethyl methacrylate used in these examples. However, it will generally be more convenient to use SiH functional silanes which also contain hydrolyzable functionality to prepare norbornene functional silanes which also include one, two or three hydrolyzable groups bound to the silicon atom thereof:

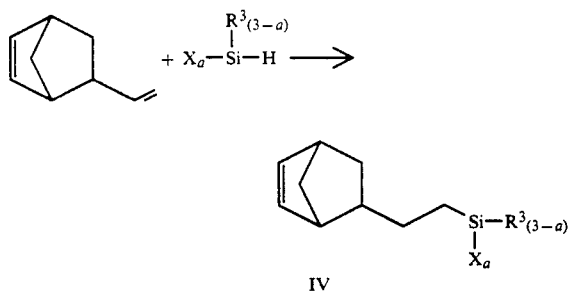

IV

Such silane compounds serve as useful monomers or capping agents for organosiloxane polymers whose molecular sizes, extent of branching and distribution of functional groups may be designed to provide specific desirable properties in the resulting norbornene functional prepolymer or in a cured polymer thereof. Examples of suitable hydrolyzable groups include chloro, methoxy, ethoxy, oxime such as methyl ethyl ketoximino, acetoxy, N,N-dialkylamino, and other hydrolyzable groups described in U.S. Pat. No. 4,699,802. For most organosiloxane polymerization or capping reactions methoxy or chloro groups will be satisfactory.

Hydrosilation catalysts are well known to those skilled in the art. Examples are platinum, chloroplatinic acid, hydrocarbon platinum complexes, rhodium complexes, etc. Platinum based catalysts, such as Karstedt catalyst and chloroplatinic acid, are preferred at levels of between 10 ppm and 500 ppm platinum, more preferably between 50 ppm and 300 ppm. The reactions can be carried out neat or in solvents which do not interfere with hydrosilations. Toluene, hexane, tetrahydrofuran, methylene chloride and benzene are examples of suitable organic solvents. The hydrosilation reactions can be followed by observing the disappearance of the SiH absorption peak at 2200 cm$^{-1}$ of the infrared spectrum. Normally the reactions are complete within three hours.

The thiolene compositions of the invention preferably comprise:

a 2-(2-norborn-5-enyl)ethyl terminated polydimethylsiloxane polymer of the formula:

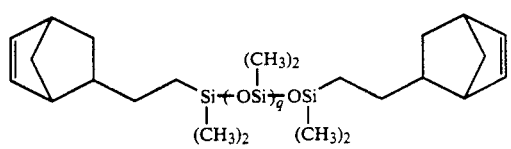

V where q is from 100–1500;

an equivalent weight amount of organosiloxane compounds having alkylthiol functionality, at least 20 percent (equivalent basis) of the polythiol being a compound of the formula:

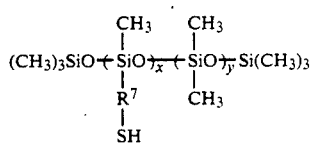

VI where $R^7$ is lower alkylene, suitably ethylene, x is 3–10 and y is 25–50; and, an initiator of thiolene addition reactions, suitably a free radical photoinitiator.

Still more preferably the polythiol component is a mixture which consists of essentially of a polythiol compound (VI) and an oligomeric dithiol chain extender of the formula:

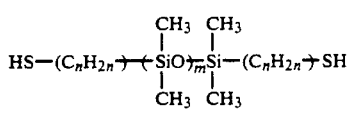

VII where m is between 1 and 3 and n is 3–15.

When cured elastomers having high elongation and low durometer values are desired, inclusion of the bis(-mercaptoalkyl)dimer in lieu of part of the polymercaptoalkylsiloxane crosslinker allows such properties to be obtained from much lower viscosity formulations. This reduces the need for high molecular weight, high viscosity components which exacerbate formulation and application difficulties.

The most preferable values are as follows:
V: q is 380
VI: x is 5 and y is 30
VII: n is 3 or 4 and m is 1
Photoinitiator: 1.5 wt% diethoxyacetophenone.

Best results are obtained when the composition conforms to the the following constraint:

norbornene equivalents = (thiol equivalents of VI + thiol equivalents of VII).

Suitably component VII is 1,3-bis(3-mercaptopropyl)-1,1,3,3-tetramethyldisiloxane, which may be prepared by a modification of a typical 3-mercaptopropyltrimethoxysilane synthesis. 1,3-Bis(3-chloropropyl)-1,1,3,3-tetramethyldisiloxane may be reacted with thiourea and ammonia to give the aforementioned product.

Capping reactions to produce ethyl norbornene functional silicones such as the silicones of formula V are suitably accomplished by condensing an ethylnorbornene silane having hydrolyzable functionality as in formula IV with a silanol terminated diorganosiloxane polymer of the formula:

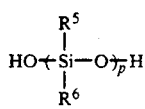   VIII where p is between 100 and about 1500 and $R^5$ and $R^6$ are the same or different organo groups. Suitable $R^5$ and $R^6$ groups are hydrocarbyl or substituted hydrocarbyl groups including alkyl such as methyl, ethyl, cyclohexyl, etc.; haloalkyl such as 3,3,3-trifluorolpropyl; and aryl which may be optionally substituted with hydrocarbon or halogen groups, especially phenyl, benzyl or methylphenyl. More preferably $R^5$ and $R^6$ are methyl or phenyl, most preferably methyl. The silanol terminated silicones typically have viscosities in the range of 500 centipoise (mPas) to 120,000 centipoise (mPas), preferably between 750 and about 50,000 centipoise (mPas), still more preferably between about 2,000 and 30,000 centipoise (mPas). The capping reaction is run in the presence of a conventional condensation catalyst, suitably a titanate, tin or tertiary amine catalyst.

Silanes of formula IV may also be used as monomers to prepare norbornene functional homopolymers and copolymers by conventional condensation polymerization procedures. Furthermore, as described in example 4 below, silanes of formula IV may also be used to prepare norbornene functional cyclic oligomeric siloxanes which likewise can be used norbornene functional siloxane polymers and copolymers by conventional methods.

The initiator used in the cureable thiolene formulations is suitably a free radical photoinitiator. Examples of free radical photoinitiators include benzoin and substituted benzoin compounds, benzophenone, Michler's ketone, dialkoxybenzophenones, dialkoxyacetophenones, peroxyesters described in U.S. Pat. Nos. 4,616,826 and 4,604,295, etc. Photosensitizers made compatible with silicones by binding photoinitiating groups to organosiloxane polymer backbones, such as the compounds disclosed in U.S. Pat. Nos. 4,477,326, 4,507,187, 4,587,276, 4,534,838 and 4,666,953 may also be used. Alternatively, thermal free radical initiators such as peroxy or azonitrile initiators can be used to cure the formulations.

Salts of complex halogenides known as cationic photoinitiators may also be used to cure the thiolene formulations. Examples of such cationic photoinitiators include di-p-tolyliodonium hexafluorophosphate, diphenyliodonium hexafluoroarsenate and UVE 1014 (trademark of General Electric Co.), a commercially available sulfonium salt of a complex halogenide.

Combinations of organic peroxides and certain $\eta^5,\eta^6$-iron arene complex compounds as described in U.S. Pat. No. 4,808,638, incorporated herein by reference, may also be employed as photoinitiators.

Typically the cureable formulations of the invention will also include one or more fillers. Suitable fillers are reinforcing glass fiber or silica fillers. Particularly preferred are fumed silicas, especially fumed silicas which have been treated to render them hydrophobic. Such silicas can be added at high levels, sometimes 60% or more, while maintaining practical viscosities. Especially preferred are silicas treated to give low thixotropic ratios such as Wacker-Chemie HDK-2000 ™. For most applications such fillers will desireably be employed at levels between about 1% and 60%, suitably between about 10% and 40%.

Inert or semi-reinforcing fillers may also be employed such as ground quartz, calcium carbonate, talc, clay and their treated counterparts, as well as other materials well known in the art. Levels of such fillers, when used, are typically 5%-60% based on the total weight of the formulation.

Although silicon hydride functional compounds will selectively hydrosilate the side unsaturated groups of the norbornene starting compounds under the conditions described herein, the ring unsaturation is reactive to hydrosilations. Thus, the norbornene functional polyorganosiloxanes of the invention may alternatively be cured using a conventional hydrosilation cure system. In such systems hydrosilation catalysts and their concentrations are as previously described for the synthesis of the norbornene functional polyorganosiloxane. The silicon hydride functional compound, however, is a polyorganosiloxane compound having a plurality of SiH groups, preferably one which includes more than two SiH groups per molecule. Example 8 illustrates this type of hydrosilation cureable formulation.

While a cureable composition using norbornene functional silicones of the invention may include both difunctional norbornenyl silicones and either a difunctional SiH or a disfunctional alkylthiol silicone, it will be understood that at least a portion of at least one of these components should contain more than two functional groups per molecule to produce a crosslinked product when cured. That is, the total of the average number of norbornene groups per molecule of norbornene functional prepolymer and the average number of coreactive groups (thiol or SiH) per molecule of the coreactive prepolymer should be greater than 4 when crosslinked cured product is desired.

The invention is illustrated by the following nonlimiting examples.

EXAMPLE 1

2-(Norborn-5-enyl)ethyltrichlorosilane

5-Vinyl-2-norbornene (1.23M, 148 g) was stirred under nitrogen at 75° C. in a round-bottomed flask equipped with a condenser and a pressure equalizing addition funnel. Trichlorosilane (0.616M, 83.11 g) was added dropwise and Karstedt catalyst (0.23 g) was quickly added. The rate of addition was adjusted to maintain a 75°-80° C. pot temperature without external heating. When addition was complete, the reaction mixture was aged at 75° C. for three hours. Infrared analysis indicated no silane was present. The reaction mixture was then concentrated on a rotary evaporator and distilled in vacuo (bp 55°–62° C., 0.05 mm Hg). Yield 143.4 g (91% theory, >95% purity by GLPC).

Similar results are obtained when chloroplatinic acid is used as the catalyst.

EXAMPLE 2

2-(Norborn-5-enyl)ethyldimethylchlorosilane

5-Vinyl-2-norbornene (4.20M, 504 g) was stirred under nitrogen at 70–°75° C. in a round-bottomed flask equipped with a thermometer, an efficient condenser and a constant pressure addition funnel. Dimethylchlorosilane (2.8M, 264 g) was added dropwise and a Karstedt catalyst (0.77 g) was added to the reaction mixture. When the addition was complete, the reaction mixture was aged at 70° C. for two hours. Analysis of the reaction indicated no silane present (FT-IR). The mixture was then stripped on a rotary evaporator and distilled in vacuo (bp 60°–64° C., 0.05 mm Hg). Yield 493 g (82% theory, 94% purity by GLPC).

EXAMPLE 3

Ethyl Norbornene capped polyorganosiloxane

Silanol fluid, Rhone Poulenc 48V3500, (0.092 eq OH) was stirred under nitrogen and warmed to 70° C. with triethylamine-dimethylaminopyridine (1.05 eq, 1% DMAP by weight). The product of example 2 (0.0956 eq, 20.5 g) was added. The reaction mixture was stirred at 75° C. for three hours then methanol (50 g) was added slowly. After one hour, volatiles were removed by concentration on a rotary evaporator, the reaction mixture was diluted with hexane and filtered through diatomaceous earth. Removal of solvent on a rotary evaporator at 75° C. (0.1 mm Hg) gave the product: Viscosity 4680 cps, GPC $MW_{wt}$ 30787, $M_{number}$ 23943.

EXAMPLE 4

Norbornene Cyclic Tetramer

Water (200ml, 11.1 moles) was added dropwise to 200.0 g, 0.85 mole, 2-(norborn-5-enyl)ethyldichloromethylsilane in 200 ml THF in a 1 liter 3-necked flask with thermometer and mechanical stirrer, allowing gentle THF reflux at 65° C. during the addition. The contents were stirred at 70° C. for one hour after the addition, then allowed to phase. The upper product layer was separated, then added to 100 g water and 50 g potassium carbonate with stirring for one hour at 70° C. After allowing to phase, the upper, product layer was removed, concentrated on a rotary evaporator, rediluted with an equal volume of hexane and filtered through a Celite ® pad. The product was isolated by rotary evaporation, giving 160.4 g of a hazy, light yellow oil (89% Theory, $MW_{wt}$=735, $MW_{number}$=607 by GPC, absence of SiOH confirmed by IR). Brookfield Viscosity: 14,300 cps (RV4 spindle, 5 rpm).

EXAMPLE 5

Using a premixed base of the product of example 3 with 35% HDK 2000 TM silica and 1.5% diethoxyacetophenone (DEAP), the inventors combined various thiol equivalent percent (eq%) increments of 3K5M (a polythiol of formula B where x is about 5 and y is about 30) and 1,3-bis(3-mercaptopropyl)-1,1,3,3-tetramethyldisiloxane (a polythiol of formula VII referred to herein as "C") adding up to the total unsaturation in the premix.

The formulations were cast between polyethylene-backed 6" square steel plates with a 70 mil by 6" square outer dimension by 5⅜" square inner dimension steel spacer. The polyethylene-backed specimens were clamped between two 6" square glass plates and placed in a Technocure TM high pressure mercury vapor lamp UV curing chamber and irradiated 60 seconds per specimen side at an intensity of 70 milliwatts per square centimeter. After cooling, the cured specimen was peeled free of the plates and cut into tensile and tear test specimens per ASTM Method D412. The following bulk properties were obtained on the test specimens:

TABLE I

EFFECT OF 1,3-BIS(3-MERCAPTOPROPYL)-1,1,3,3-TETRAMETHYLDISILOXANE

| | Amounts of C | | | |
|---|---|---|---|---|
| | 20 eq % | 40 eq % | 60 eq % | 80 eq % |
| Premix | 150 g | 150 g | 150 g | 150 g |
| 3K5M | 5.8 g | 4.3 g | 2.9 g | 1.45 g |
| (C) | 0.3 g | 0.6 g | 0.9 g | 1.2 g |
| Tensile (psi) | 1215 | 1254 | 931 | 269 |
| Elongation (%) | 454 | 589 | 701 | 630 |
| Tear (pli) | 218 | 231 | 186 | 37 |
| Shore A | 40 | 37 | 27 | 13 |
| % Extractables | 4.5 | 6.3 | 8.1 | 16.5 |

These data indicate that nearly equiequivalent amounts of 3K5M and the oligomeric siloxane dithiol "C" offer the best elongation improvement versus extent of cure. The 80 eq% point, illustrates the effects of very low crosslink density in this system, evidenced by the low Shore A. Cured properties without any (C) are very similar to the 20 eq% point.

It is readily apparent that (C) adds additional flexibility to the above formulations.

EXAMPLE 6

The propargyl ester of 2-norborn-5-ene carboxylic acid was prepared by Diels-Alder reaction of propargyl acrylate and cyclopentadiene at ambient temperature. Dimethylchlorosilane (56.4g) was added portionwise to 100 grams of this norbornene carboxylate ester and 0.16 g Karstedt catalyst under nitrogen at 70° C. After exotherming to 80° C., the mixture was stirred for 3 hours at 70° C., stripped under light vacuum and then distilled. The product,

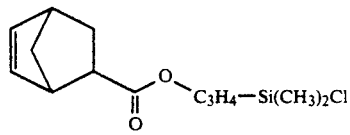

(84% purity by GC), distilled at 100°–105° C. at 0.07 mm.

EXAMPLE 7

A mixture of allyl alcohol (116 g, 2.0 mol), triethylamine (202 g, 2.0 mol) and 4-dimethylaminopyridine (2.44 g, .02 mol) in benzene (500 ml) was stirred at 51° C. in a 2 liter three-necked flask equipped with a mechanical stirrer, a thermometer, and a pressure equalizing addition funnel under a nitrogen atmosphere. A solution of norborn-5-ene-2-carboxylic acid chloride (197 g, 1.26 mol) in benzene (100 ml) was added dropwise so that the temperature of the reaction did not exceed 20° C. during the addition. When the addition was complete, the viscous slurry was warmed to 55° C. and aged at this temperature for one hour. The reaction mixture was then cooled to room temperature and filtered. The filter cake was washed successively with pentane (2 times 200 ml) and ether (2 times 200 ml). The filtrate was then concentrated on a rotary evaporator and distilled in vacuo (bp 85°-93° C., at 0.2-0.1 mm Hg). The yield of distilled product was 201 g and consisted of a mixture of endo and exo isomers of allyl norborn-5-ene-2-carboxylate. The purity of the product was judged to be >98% by gas chroatographic analysis.

Chlorodimethylsilane (26.6 g, 0.281 mol) was slowly at 80° C. to 50.0 g (0.281 mol) allyl norborn-added 5-ene-2-carboxylate and 0.16 g Karstedt catalyst (50 ppm Pt) in 100 ml toluene under a nitrogene blanket. No exotherm was observed, even with complete addition of chlorodimethylsilane. After heating and stirring 18 hours at 80° C., IR confirmed the disappearance of SiH. After briefly stripping on a rotary evaporator, a small quantity of precipitate formed, which was removed by dilution with an equal volume of heptane, and filtering. After reconcentrating, the crude product was vacuum distilled, removing a forecut at 50°-90° C. at 0.06 mm, followed by the product at 90°-92° C. at 0.06 mm. Yield: 30.6 g (40%) of a slightly cloudy liquid. MNR analysis confirmed the product as:

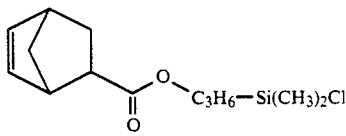

with no evidence of silane addition to the internal ring norbornene double bond.

EXAMPLE 8

One hundred grams of an ethylnorbornene capped polyorganosiloxane as prepared in Example 3 was mixed in a 250 ml beaker with 3.91 gm of a SiH functional polydimethylsiloxane having an average of 7 SiH groups per molecule and an SiH equivalent wt. of 346, and a catalytic amount of Karstedt catalyst (0.1 gm). The liquid mixture gelled within 3 hours and produced a rubbery elastomeric solid easily removable from the beaker after 24 hours at ambient temperature.

What is claimed is:

1. An organosiloxane polymer containing a plurality of groups of the formula:

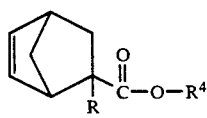

bound to silicon atoms thereof, where R is H or methyl and $R^4$ is ethylene, ethenylene, propylene or propenylene, said polymer being substantially free of groups of the formula:

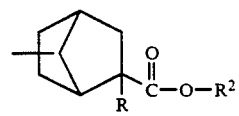

bound to silicon atoms thereof where $R^2$ is vinyl, ethynyl, allyl or propargyl.

2. A polymer as in claim 1 wherein $R^4$ is a propylene or propenylene group.

3. An organosiloxane polymer comprising the condensation reaction product of a compound of the formula:

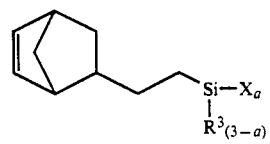

where X is a hydrolyzable group, a is 1-3 and $R^3$ is hydrocarbyl, with a silanol terminated polyorganosiloxane of the formula:

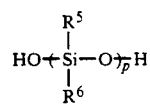

where p is between 100 and about 1500 and $R^5$ and $R^6$ are the same or different organo groups.

4. A polymer as in claim 3 wherein the silanol terminated polyorganosiloxane has a viscosity of between 2,000 and 30,000 centipoise.

5. A polymer as in claim 4 wherein the $R^5$ and $R^6$ groups are methyl.

6. A compound having the formula:

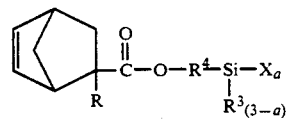

in substantially pure form where X is a hydrolyzable group, a is 1-3, R is H or methyl, $R^3$ is hydrocarbyl and $R^4$ is ethylene, ethenylene, propylene or propenylene.

7. A compound as in claim 6 wherein $R^4$ is a propylene or propenylene group.

8. A compound as in claim 6 having the formula:

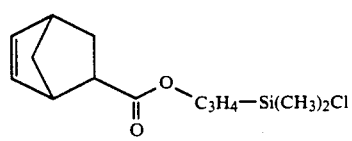

or

9. A process comprising the steps of:

i) reacting a norbornene compound of the formula:

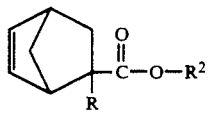

where R is H or methyl and $R^2$ is vinyl, ethenyl, allyl or propargyl, with a silicon hydride functional compound of the formula:

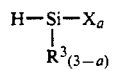

where X is a hydrolyzable group, a is 1–3 and $R^3$ is hydrocarbyl, in the presence of a platinum based or rhodium hydrosilation catalyst at a temperature of at least 60° C.; and ii) recovering a product which consists essentially of the addition products of the silicon hydride functional compound to the $R^2$ group of the norbornene compound and which is substantially free of addition products of the silicon hydride functional compound to the internal ring double bond of the norbornene compound.

10. A polymer as in claim 9 wherein $R^3$ is selected from the group consisting of chloro, methoxy, ethoxy, oxime, acetoxy and N,N-dialkylamino.

* * * * *